United States Patent [19]
Wess et al.

[11] Patent Number: 5,641,767
[45] Date of Patent: Jun. 24, 1997

[54] MODIFIED BILE ACIDS PROCESS FOR THEIR PREPARATION AND THEIR USE

[75] Inventors: Günther Wess, Erlensee; Alfons Ehnsen, Büttelborn; Werner Kramer, Mainz; Klaus Bock, Hattersheim, all of Germany

[73] Assignee: Hoechst Aktiengesellschaft, Frankfurt am Main, Germany

[21] Appl. No.: 525,231

[22] Filed: Sep. 12, 1995

[30] Foreign Application Priority Data

Sep. 14, 1994 [DE] Germany .................. 44 32 708.0

[51] Int. Cl.$^6$ .................. A61K 31/58; A61K 31/575; C07J 9/00
[52] U.S. Cl. .................. 514/172; 514/182; 540/4; 540/114
[58] Field of Search .................. 552/505, 554, 552/555, 553; 514/172, 182; 540/4, 114

[56] References Cited

U.S. PATENT DOCUMENTS

| | | | |
|---|---|---|---|
| 4,337,206 | 6/1982 | Gargani | 260/397.1 |
| 4,379,093 | 4/1983 | Bonaldi et al. | 260/397.1 |
| 4,834,919 | 5/1989 | Magni et al. | 260/397.1 |
| 5,095,130 | 3/1992 | Vivat et al. | 552/553 |
| 5,500,421 | 3/1996 | Parenti | 514/182 |
| 5,508,453 | 4/1996 | Aresio et al. | 552/553 |
| 5,565,587 | 10/1996 | Aiosio et al. | 552/554 |

FOREIGN PATENT DOCUMENTS

| | | |
|---|---|---|
| 0 417 725 A2 | 3/1991 | European Pat. Off. . |
| 489 423 A1 | 6/1992 | European Pat. Off. . |
| 0548793 | 6/1993 | European Pat. Off. . |
| 0 573 848 A2 | 12/1993 | European Pat. Off. . |

OTHER PUBLICATIONS

Wess, et. et al., "Modified Bile Acids: Preparation of 7α, 12α–Dihydroxy–3β–and 7α, 12α–Dihydroxy–3α(2–Hydropxyethoxy)–5β–Cholanic Acid and Their Biological Activity," *Tetrahedron Letters*, vol. 33, No. 2, 1992, pp. 195–198.

Kramer et al., "Liver–Specific Drug Tareting by Coupling to Bile Acids", *The Journal of Biological Chemistry*, 267(26):18598–18604 (1992).

G. Wess et al., "Specific Inhibitors of Ileal Bile Acid Transport", *Journal of Medicinal Chemistry*, 37(7):873–875 (1994).

*Primary Examiner*—Kimberly J. Prior
*Attorney, Agent, or Firm*—Finnegan, Henderson, Farabow, Garrett & Dunner, L.L.P.

[57] ABSTRACT

The invention relates to linker-modified bile acid derivatives of the formula I:

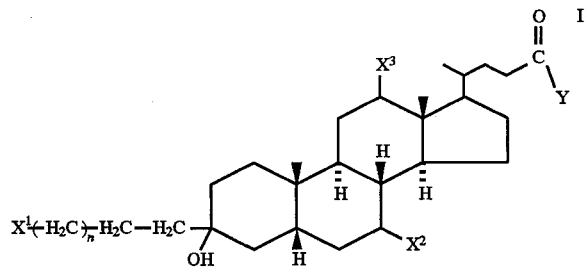

wherein the radicals $X^1$, $X^2$, $X^3$ and Y and n are as defined in the claims, and to a process for their preparation. The compounds according to the invention are therapeutically active and are thus suitable as drugs, especially as hypolipldemics. The invention further relates to the use of the bile acid derivatives according to the invention as drugs.

6 Claims, No Drawings

MODIFIED BILE ACIDS PROCESS FOR THEIR PREPARATION AND THEIR USE

Bile acids with linker structures in steroidal positions C-3, C-7 and C-12 are of interest for pharmaceutical applications. Thus, by coupling active substances with bile acids via suitable linkers, it is possible to achieve a liver-specific active substance uptake and hence a pharmacological action or to improve the absorption of poorly absorbed drugs such as peptides (see e.g. Kramer et al., J. Biol. Chem., 267: 18598–18604, 1992; Kramer et al., J. Biol. Chem., 269: 1–7, 1994; European patent application EP-A-0 417 725 (corresponds to U.S. patent application Ser. No. 08/208,192)). The coupling of bile acids via linker structures produces bile acid absorption inhibitors (see e.g. Wess et al., J. Med. Chem., 37: 873, 1994; European patent applications EP-A-0 573 848 (corresponds to U.S. patent application Ser. No. 08/074,753) and EP-A-0 489 423).

In the state of the art, it is described that for these applications it is possible to use modified bile acids which do not have a 3-OH group on the carbon atom carrying the linker. Because of the lack of starting materials for the preparation of compounds with variable linkers and functionalities in the end position of the linker, and because of the simultaneous presence of an OH group at the coupling site of the linker with the bile acid moiety (3-C), these compounds are not yet known.

It has been found that the compounds of the formula I according to the invention are accessible by the direct coupling of a suitable acetylene derivative with a suitable bile acid ketone. It has further been found that a number of chemical conversions can be performed on these primary addition products and their secondary products without the presence of the OH group at the coupling site causing troublesome side reactions.

The invention relates to linker-modified bile acid derivatives of the formula I:

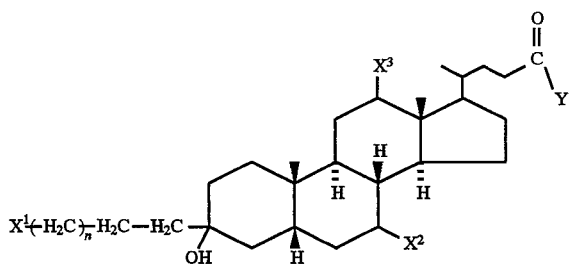

wherein $X^1$ is

| | |
|---|---|
| $CH_2OH$, | |
| $CH_2NH_2$, | |
| $CH_2OSil$, | where Sil is a silyl protecting group of the formula |
| | $SiMe_3$, |
| | $SiMe_2t$-Bu or |
| | $SiPh_2t$-Bu, |
| $CH_2OTHP$, | where phenyl can be substituted by |
| $CH_2OCH_2Ph$, | p-methoxy, |
| $CH_2O$-trityl, | where acyl is a linear or branched |
| $CH_2O$-acyl, | radical having 2 to 8 carbon atoms, |
| $CH_2O$-benzoyl, | where the aromatic ring can also be monosubstituted to trisubstituted by a linear or branched $C_1$-$C_4$-alkyl radical, $OCH_3$, F or Cl, |
| $CH_2OCHO$, | where acyl is a linear or branched |
| $CH_2OC(O)OCH_2Ph$, | radical having 2 to 8 carbon atoms, |
| $CH_2NH$-acyl, | |
| $CH_2NH$-benzoyl, | where the aromatic ring can also be monosubstituted to trisubstituted by a linear or branched $C_1$-$C_4$-alkyl radical, $OCH_3$, F or Cl, |
| $CH_2N(CH_2Ph)_2$, | where the aromatic rings can also be monosubstituted to trisubstituted by a linear or branched $C_1$-$C_4$-alkyl radical, $OCH_3$, F or Cl, |
| $CH_2O$—$CH_2$—$CH$=$CH_2$, | where M is an |
| $CO_2H$, $CO_2M$, | alkali metal or alkaline earth metal, |
| $CO_2N(X^4)_4$, | where $X^4$ is identical or different and is an H atom or a linear or branched alkyl radical having 1 to 8 carbon atoms, |
| $CO_2X^5$, | where $X^5$ is methyl, ethyl, alkyl or benzyl; |

$X^2$ and $X^3$ are identical or different radicals selected from the group comprising

| | |
|---|---|
| H, OH, OTHP, OAc, | where the phenyl group can also be |
| $SiMe_3$, $OSiMe_2t$-Bu, | monosubstituted to trisubstituted by a |
| $SiPh_2t$-Bu, $OCH_2Ph$, | linear or branched $C_1$-$C_4$-alkyl radical, $OCH_3$, F or Cl, |
| O—$CH_2CH$=$CH_2$, | where the phenyl group can also be |
| $OC(O)CH_2Ph$, | monosubstituted to trisubstituted by a linear or branched $C_1$-$C_4$-alkyl radical, $OCH_3$, F or Cl, |
| $OC(O)Ph$, | where the phenyl group can also be monosubstituted to trisubstituted by a linear or branched $C_1$-$C_4$-alkyl radical, $OCH_3$, F or Cl, |
| or | |
| $OC(O)O$-alkyl, | | the radical $X^2$ being located in the α- or β-position and the radical $X^3$ only in the α-position;

Y is

| | |
|---|---|
| OH, | a linear or branched alkoxy radical having 1 to 8 carbon atoms, |
| O—$CH_2Ph$, | where the phenyl group can also be monosubstituted to trisubstituted by a linear or branched $C_1$-$C_4$-alkyl radical, $OCH_3$, F or Cl, |
| O-Ph, | where the phenyl group can also be monosubstituted to trisubstituted by a linear or branched $C_1$-$C_4$-alkyl radical, $OCH_3$, F or Cl, |
| $OM^1$, | where $M^1$ is an alkali metal, |
| $ONX_4^6$, | where $X^6$ is an H atom or a $C_1$-$C_8$-alkyl group, |
| OTHP, | |
| $OCH_2$—$CH$=$CH_2$, | |
| $NH_2$, | |
| $NH(CH_2)_2SO_3H$, | |
| $N(CH_3)(CH_2)_2SO_3H$, | |
| $NHCH_2CO_2H$ or | |
| $N(CH_3)CH_2CO_2H$; | | the hydroxyl group in ring position C-3 can be located in either the α- or β-position and n is equal to 0 to 47.

Preferred linker-modified bile acid derivatives of the formula I are those wherein $X^1$ is $CH_2OH$,
$CH_2NH_2$,
$CH_2OSiMe_2t$-Bu,
$CH_2OTHP$,
$CO_2H$ or
$CO_2CH_3$;

$X^2$ and $X^3$ are identical or different radicals selected from the group comprising H,
OH,
OAc and OTHP,
the radical $X^2$ being located in the α- or β-position and
the radical $X^3$ only in the α-position;

Y is

OH,
$OCH_3$ or
Ot-Bu;

the hydroxyl group in ring position C-3 is preferably located in the α-position and n is equal to 0 to 47.

The linker-modified bile acid derivatives of the formula I according to the invention are all the stereoisomeric forms and physiologically acceptable salts of these compounds.

THP is understood as meaning a tetrahydropyranyl group. Me, t-Bu and Ac denote methyl, tertiary butyl and acetyl respectively. Trityl stands for triphenylmethyl.

The invention further relates to a process for the preparation of the compounds according to the invention, wherein, basically in accordance with Scheme 1, a suitable bile acid ketone II, which is known from the literature, obtained commercially or prepared in accordance with Scheme 2 and wherein $X^2$, $X^3$ and Y are radicals as in the formula I, is coupled with a suitable acetylene derivative III, which is known from the literature or prepared in accordance with Scheme 3 and wherein $X^1$ is a radical as in the formula I and n is equal to zero to 47, to give an addition product IV, wherein $X^1$, $X^2$, $X^3$ and Y are radicals as in the formula I and n is equal to zero to 47. In this coupling reaction, the acetylene derivative III has first been converted to the corresponding lithium derivative with a strong base, e.g. an alkyl-lithium compound. The primary addition product IV, in which the radicals $X^1$, $X^2$, $X^3$ and Y are radicals as in the formula I and n is equal to zero to 47, is converted by catalytic hydrogenation to the corresponding saturated compound I and, if appropriate, by further conversions, such as elimination of protecting groups and conversion of functional groups, to other compounds of the formula I according to the invention, wherein $X^1$, $X^2$, $X^3$ and Y are radicals as in the formula I and n is equal to zero to 47. In this reaction sequence, the radicals according to the invention must be chosen so that no troublesome side reactions occur, as shown below by way of example (Scheme 2).

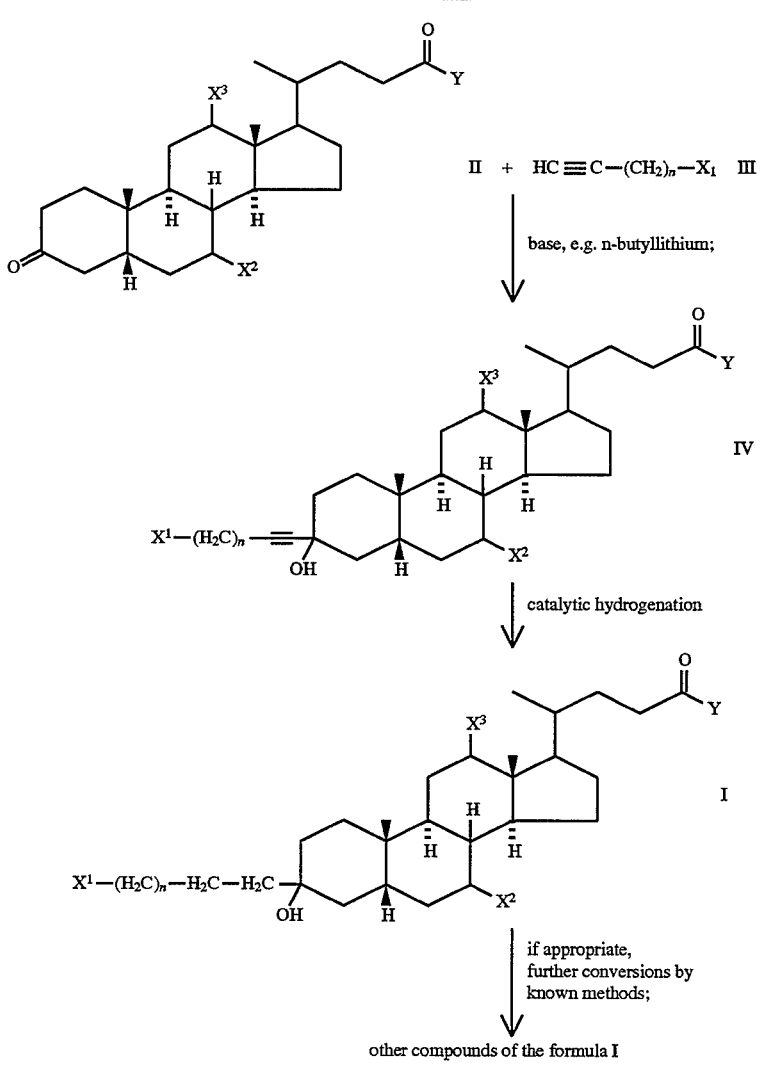

Scheme 1

Scheme 2 shows, by way of example, the preparation of compounds according to the invention where n=3; $X^2=X^3=$OTHP, OH; $X^1=CH_2OH$, $CH_2NH_2$, $CO_2H$. In the reaction sequences starting from compound I (e), it is shown how one compound of the formula I according to the invention can be converted to other compounds of the formula I according to the invention.

In the reaction of the THP-protected methyl 3-ketocholate (compound II (c)) with hex-5-yn-1-ol, the alcohol group was not protected but converted to the lithium alcoholate intermediate with a second equivalent of n-butyllithium. In the case of long-chain alkynols where n≧6, the OH groups were preferably protected as t-butyldimethylsilyl ethers.

It was found, surprisingly, that long-chain alkynols or the corresponding t-butyldimethylsilyl ethers add onto ketones in particularly high yield if the lithium acetylide is generated with n-butyllithium at elevated temperature, preferably under reflux.

In Scheme 2:

p-TosH denotes p-toluenesulfonic acid

THF denotes tetrahydrofuran

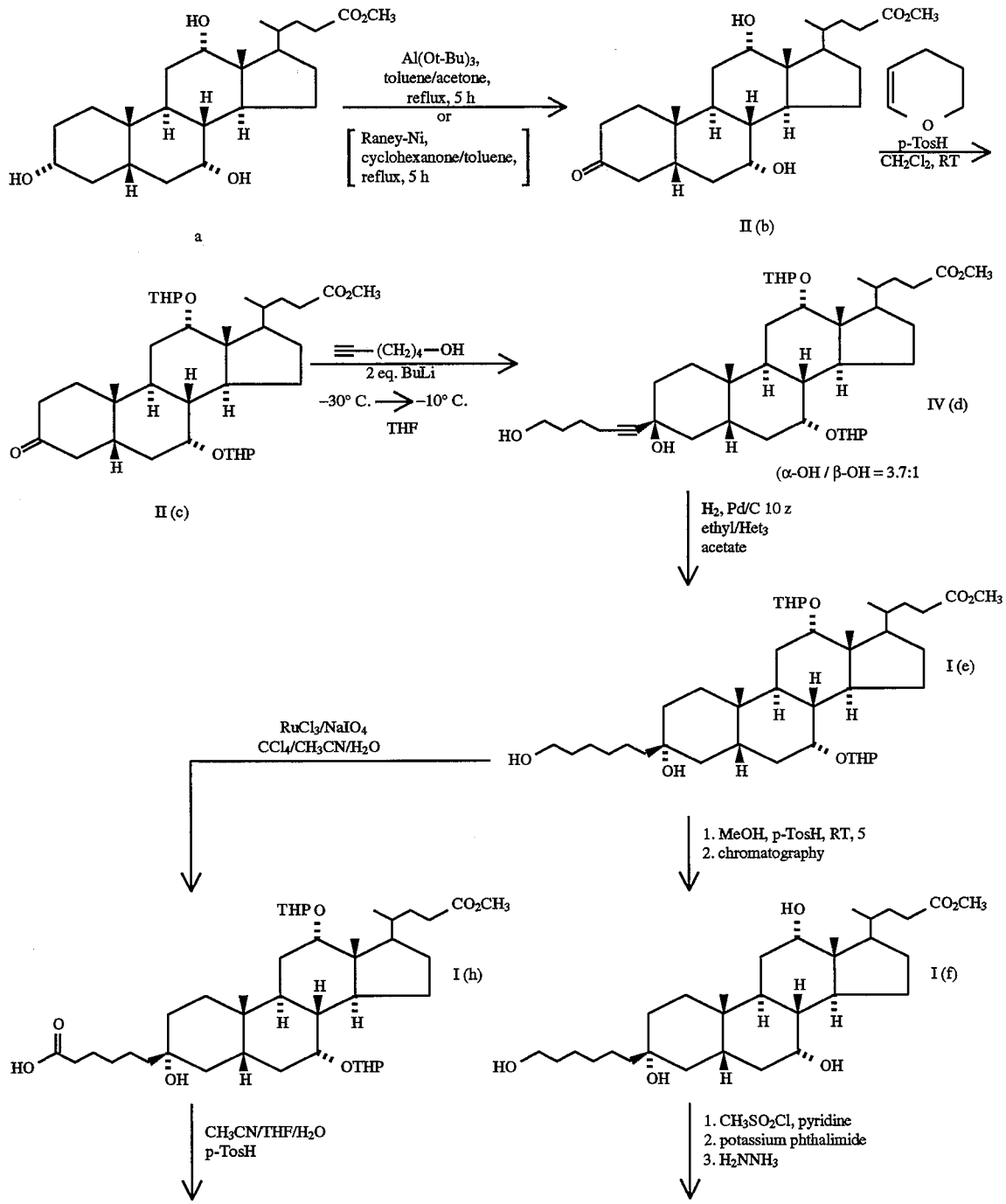

-continued
Scheme 2

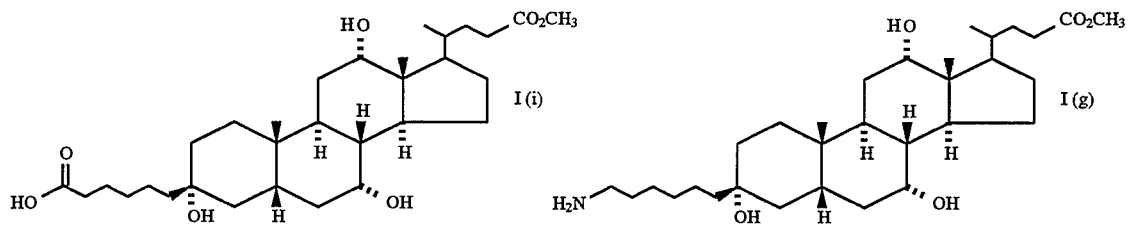

If the alkynols are not obtainable commercially, they are prepared on the basis of literature processes in accordance with Scheme 3. This process is applicable to alkynols which are used in the process according to the invention and which have the required chain length in each case. The key step is the isomerization of a triple bond into the ω-terminal position under the indicated reaction conditions.

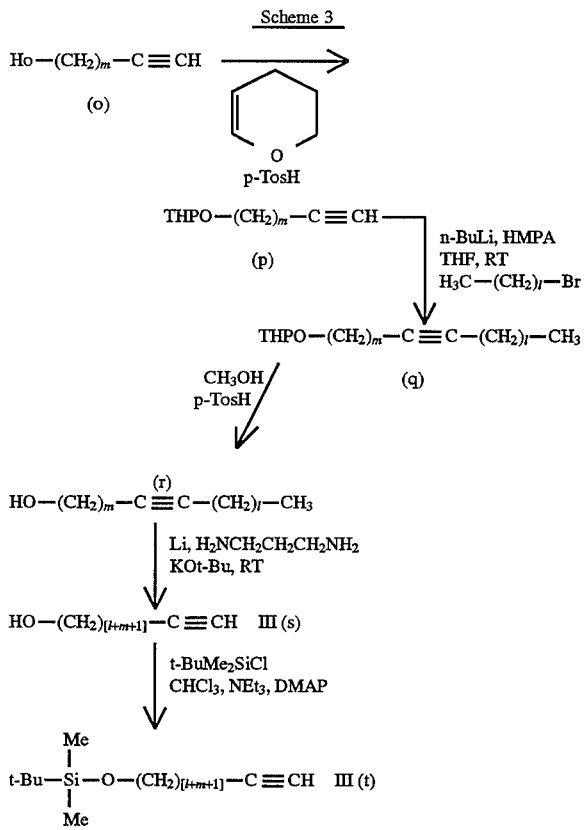

In Scheme 3:
HMPA denotes hexamethylphosphoric triamide
DMAP denotes 4-dimethylaminopyridine
Also, n=l+m.

The compounds of the formula I according to the invention possess valuable pharmacological properties. The invention therefore also relates to drugs containing at least one compound of the formula I according to the invention, and to the use of the compounds of the formula I as drugs, especially for lowering a raised lipid level.

For the preparation of a drug containing at least one compound of the formula I, the compounds of the formula I are dissolved or suspended in pharmacologically acceptable organic solvents such as monohydric or polyhydric alcohols, e.g. ethanol or glycerol, triacetin, oils, e.g. sunflower oil or cod-liver oil, ethers, e.g. diethylene glycol dimethyl ether, or polyethers, e.g. polyethylene glycol, or else in the presence of other pharmacologically acceptable polymeric excipients, e.g. polyvinylpyrrolidone, or other pharmaceutically acceptable additives such as starch, cyclodextrin or polysaccharides. The compounds according to the invention can also be administered in combination with other medicinal substances.

The compounds of the formula I are administered in various dosage forms, preferably orally in the form of tablets, capsules or liquids. The daily dose ranges from 3 mg to 5000 mg, depending on the patient's body weight and constitution, but preferably ranges from 10 to 1000 mg.

The biological testing of the compounds according to the invention was carried out by determining the inhibition of [$^3$H]-taurocholate uptake into rabbit ileum brush border membrane vesicles. The inhibition test was performed as follows:

1. Preparation of rabbit ileum brush border membrane vesicles

Brush border membrane vesicles were prepared from the cells of the small intestine by the so-called $Mg^{2+}$ precipitation method. Male New Zealand rabbits (body weight 2 to 2.5 kg) were sacrificed by the intravenous injection of 0.5 ml of T61®, which is an aqueous solution of 2.5 mg of tetracaine hydrochloride, 100 mg of embutramide and 25 mg of mebezonium iodide. The small intestine was removed and rinsed with ice-cold isotonic solution. The terminal 7/10 of the small intestine (measured in the oral to rectal direction, i.e. the terminal ileum, which contains the active $Na^+$-dependent bile acid transport system) were used to prepare the brush border membrane vesicles. The intestines were frozen in plastic bags under nitrogen at −80° C. To prepare the membrane vesicles, the frozen intestines were thawed at 30° C. in a water bath. The mucosa was scraped off and suspended in 60 ml of ice-cold 12 mM Tris/HCl buffer (pH 7.1)/300 mM mannitol, 5 mM EGTA/10 mg/1 phenylmethylsulfonyl fluoride/1 mg/l trypsin inhibitor from soya beans (32 U/mg)/0.5 mg/l trypsin inhibitor from bovine lung (193 U/mg)/5 mg/l bacitracin. The suspension was diluted to 300 ml with ice-cold distilled water and then homogenized with an Ultraturrax (no. 18 rotor, IKA Werk Staufen, Germany) for 3 minutes at 75% max. power, with ice cooling. After the addition of 3 ml of 1M $MgCl2$ solution (final concentration 10 mM), the homogenate was left to stand for exactly i minute at 0° C. The addition of $Mg^{2+}$ causes the cell membranes to aggregate and precipitate, with the exception of the brush border membranes. After centrifugation for 15 minutes at 3000× g (5000 rpm, SS-34 rotor), the precipitate is discarded and the supernatant, which contains the brush border membranes, is centrifuged for 30 minutes at 48,000× g (20,000 rpm, SS-34 rotor). The supernatant was discarded and the precipitate was rehomogenized in 60 ml of 12 mM Tris/HCl buffer (pH 7.1)/60 mM mannitol, 5mM EGTA with a Potter Elvejhem homogenizer (Braun, Melsungen, 900 rpm, 10 strokes). After the addition of 0.1 ml of 1M $MgCl_2$ solution and incubation for 15 minutes at 0° C., the homogenate was centrifuged again for 15 minutes at 3000× g. The supernatant was then centrifuged for a further 30 minutes at 48,000× g (20,000 rpm, SS-34 rotor). The precipitate was taken up in 30 ml of 10 mM Tris/Hepes buffer (pH 7.4)/300 mM mannitol and homogeneously resuspended by 20 strokes in a Potter Elvejhem homogenizer at 1000 rpm. After centrifugation for 30 minutes at 48,000× g (20,000 rpm, SS-34 rotor), the precipitate was taken up in 0.5 to 2 ml of Tris/Hepes buffer (pH 7.4)/280 mM mannitol (final concentration 20 mg/ml) and resuspended using a tuberculin syringe with a 27 gauge needle. The vesicles were either used immediately after preparation for transport studies or stored in 4 mg portions at –196° C. in liquid nitrogen.

2. Inhibition of Na+-dependent [$^3$H]-taurocholate uptake into ileum brush border membrane vesicles The uptake of substrates into the above-described brush border membrane vesicles was determined by the so-called membrane filtration technique. 10 µl of the vesicle suspension (100 µg of protein) were pipetted dropwise onto the wall of a polystyrene incubation tube (11×70 mm) containing the incubation medium with the appropriate ligands (90 µl). The incubation medium contained 0.75 µl=0.75 µCi of [$^3$H(G)]-taurocholate (specific activity: 2.1 Ci/mmol)/0.5 µl of 10 mM taurocholate/8.75 µl of sodium transport buffer (10 mM Tris/Hepes (pH 7.4)/100 mM mannitol/100 mM NaCl) (Na—T—B) or 8.75 µl of potassium transport buffer (10 mM Tris/Hepes (pH 7.4)/100mM mannitol/100 mM KCl) (K—T—B) and 80 µl of the inhibitor solution in question, dissolved in Na—T—B or K—T—B according to the experiment. The incubation medium was filtered through a polyvinylidene fluoride membrane filter (SYHV LO 4NS, 0.45 µm, φ4 mm, Millipore, Eschborn, Germany). The transport measurement was started by mixing the vesicles with the incubation medium. The concentration of taurocholate in the incubation mixture was 50 µm. After the desired incubation time (conventionally 1 minute), the transport was stopped by the addition of 1 ml of ice-cold stop solution (10 mM Tris/Hepes (pH 7.4)/150 mM KCl). The mixture formed was immediately filtered with suction under a vacuum of 25 to 35 mbar through a cellulose nitrate membrane filter (ME 25, 0.45 µm, diameter 25 mm, Schleicher & Schuell, Dassell, Germany). The filter was rinsed with 5 ml of ice-cold stop solution.

For measurement of the uptake of radiolabeled taurocholate, the membrane filter was dissolved with 4 ml of Quickszint 361 scintillator (Zinsser Analytik GmbH, Frankfurt, Germany) and the radioactivity was measured by liquid scintillation in a TriCarb 2500 instrument (Canberra Packard GmbH, Frankfurt, Germany). After calibration of the instrument using standard samples and after correction for any chemiluminescence present, the measured values were obtained as dpm (disintegrations per minute).

The control values were determined in both Na—T—B and K—T—B. The difference between the uptakes in Na—T—B and K—T—B gave the Na+-dependent transport. $IC_{50}$ Na$^+$ was used to designate the concentration of inhibitor at which the Na$^+$-dependent transport was inhibited by 50%, based on the control.

The pharmacological data comprise a test series in which the interaction of the compounds according to the invention with the intestinal bile acid transport system in the terminal small intestine was studied. The results are collated in Table 2.

Table 2 shows measured values of the inhibition of [$^3$H]-taurocholate uptake into rabbit ileum brush border membrane vesicles. It indicates the quotients of the $IC_{50}$ Na values of the reference substance as taurochenodeoxycholate (TCDC) and the particular test substance.

TABLE 2

| Compound of Example | $\dfrac{IC_{50Na} \text{ of TCDC [µmol]}}{IC_{50Na} \text{ of substance [µmol]}}$ |
| --- | --- |
| 36 (α isomer) | 0.13 |
| 36 (β isomer) | 0.13 |
| 41 | 0.16 |
| 45 | 0.12 |

1. Preparation of bile acid ketones II

EXAMPLE 1 t-Butyl cholate 100 g (0.2448 mol) of cholic acid were placed in 500 ml of tetrahydrofuran (THF). 345.8 ml (2.448 mol) of trifluoroacetic anhydride were added dropwise at 0°–5° C.

The mixture was stirred for I h at room temperature. It was then cooled to 0° C. and 459.4 ml (4.90 mol) of t-butanol were added dropwise at 0°–5° C. The mixture was stirred overnight at room temperature. 500 ml of 25% aqueous ammonium hydroxide solution were added dropwise at 0° C. and the reaction mixture was stirred for 5 h at room temperature, poured into water and extracted with ethyl acetate (3×). Drying of the combined organic phases ($Na_2SO_4$), removal of the solvent (ethyl acetate) and chromatography on silica gel (ethyl acetate/MeOH=9:1) gave 55 g (48% of theory) of t-butyl cholate.

$C_{28}H_{48}O_5$ (464.7) MS (FAB) 471M+Li

EXAMPLE 2 t-Butyl 3-ketocholate 41 g (0.088 mol) of t-butyl cholate of Example 1 were refluxed for 5 h in 600 ml of toluene/300 ml of acetone in the presence of 43.5 g (0.177 mol) of aluminum t-butylate. The reaction mixture was poured into a mixture of 2 1 of 1 molar sulfuric acid and 1 kg of ice and extracted with ethyl acetate (3×). Drying of the combined organic phases with $MgSO_4$, removal of the solvent and flash chromatography on silica gel (ethyl acetate/cyclohexane=2:1) gave 29.5 g (72% of theory) of t-butyl 3-ketocholate.

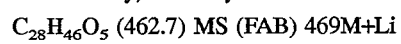

$C_{28}H_{46}O_5$ (462.7) MS (FAB) 469M+Li

EXAMPLE 3 t-Butyl 3-keto-7,12-ditetrahydropyranylcholate 1.0 g (0.0021 mol) of t-butyl 3-ketocholate of Example 2 was dissolved in 25 ml of dichloromethane. 2.5 ml of dihydropyran were added, followed by a catalytic amount (1 crystal) of p-toluenesulfonic acid monohydrate. After 3 h at room temperature, the reaction mixture was poured into saturated aqueous sodium chloride solution and extracted with dichloromethane (3×). The combined organic phases were dried ($Na_2SO_4$) and the solvent was removed. Flash chromatography on silica gel (ethyl acetate/cyclohexane= 1:4) gave t-butyl 3 -keto-7,12-ditetrahydropyranylcholate in quantitative yield.

$C_{38}H_{62}O_7$ (630.9) MS (FAB) 637M+Li

EXAMPLE 4

Methyl 3-ketocholate

Methyl 3-ketocholate was obtained from methyl cholate analogously to Example 2.

$C_{25}H_{40}O_5$ (420.5) MS (FAB) 427M+Li

EXAMPLE 5

Methyl 3-keto-7,12-ditetrahydropyranylcholate

Methyl 3-keto-7,12-ditetrahydropyranylcholate was obtained from methyl 3-ketocholate analogously to Example 3.

$C_{35}H_{56}O_7$ (588.8) MS (FAB) 595M+Li

EXAMPLE 6

Methyl 3-keto-7,12-diacetylcholate 35 g (0.0832 mol) of methyl 3-ketocholate were dissolved in 200 ml of pyridine, and 75 ml of acetic anhydride were added. The mixture was refluxed for 2 h. After cooling, the reaction mixture was added dropwise to 4 l of water. The product was filtered off with suction, washed with water and extracted by stirring with 200 ml of diisopropyl ether.

Yield: 35 g (83% of theory) of methyl 3-keto-7,12-diacetylcholate.

$C_{29}H_{44}O_7$ (504.7) MS (FAB) 511M+Li

2. Preparation of acetylene derivatives III

EXAMPLE 7

11-Tetrahydropyranyloxyundecyne 17.5 g (0,104 mol) of undec-10-yn-1-ol were dissolved in 100 ml of dichloromethane and 25 ml of dihydropyran, and a catalytic amount (spatula tipful) of p-toluenesulfonic acid monohydrate was added. The reaction mixture was left to stand overnight at room temperature and poured into saturated aqueous sodium chloride solution. Extraction with dichloromethane (3×), drying ($Na_2SO_4$) of the combined organic phases and flash chromatography on silica gel (n-heptane/ethyl acetate=10:1) gave 24 g (92% of theory) of 11-tetrahydropyranyloxyundecyne.

$C_{16}H_{24}O_2$ (252.4) MS (DCI) 253M+H

EXAMPLE 8

1-Tetrahydropyranyloxyhentriacont-10-yne 5 g (0.0198 mol) of 11-tetrahydropyranyloxyundecyne of Example 7 were placed in a mixture of 50 ml of THF and 25 ml of hexamethylphosphoric triamide under an argon atmosphere. At −60° C., 12.4 ml (0.0198 mol) of n-butyllithium in hexane were added dropwise. After 30 min at −60° C., a solution of 9.0 g (0.0248 mol) of 1-bromoeicosane in 25 ml of THF was added dropwise at −60° C. The mixture was left to warm up to room temperature. After 18 h at room temperature, it was poured into 25% aqueous $NaH_2PO_4$ solution and extracted with n-heptane (3×). The combined organic phases were dried ($Na_2SO_4$) and the solvent was removed. Flash chromatography on silica gel (n-heptane/ethyl acetate =15:1) gave 6.5 g (61.3% of theory) of 1-tetrahydropyranyloxy-hentriacont-10-yne.

$C_{36}H_{68}O_2$ (532.9) MS (DCI) 533M+H

EXAMPLE 9

Hentriacont-10-yn-1-ol 25.6 g (0.048 mol) of 1-tetrahydropyranyloxyhentriacont-10-yne of Example 8 were dissolved in a mixture of 100 ml of THF and 50 ml of methanol, and a catalytic amount (spatula tipful) of p-toluenesulfonic acid monohydrate was added at room temperature. After 3 h at room temperature, the reaction mixture was poured into 1.5 l of water and stirred for 30 min. The product was filtered off with suction, washed with water and dried under high vacuum.

Yield: 20.8 g (96% of theory) of hentriacont-10-yn-1-ol.

$C_{31}H_{60}O$ (448.8) MS (DCI) 449M+H

EXAMPLE 10

Hentriacont-30-yn-1-ol 1.0 g (0.1448 mol) of lithium wire was added in small pieces to 75 ml of propylenediamine under an argon atmosphere at room temperature. The mixture was stirred for 15 min at room temperature and then heated at 70° C. until the blue coloration had disappeared. It was cooled to room temperature, 10 g (0.0891 mol) of potassium t-butylate were added, the mixture was stirred for 15 min at room temperature and 10 g (0.0223 mol) of hentriacont- 10-yn-1-ol of Example 9 were added as a solid. The mixture was left to stand overnight at room temperature, poured into ice-water and stirred for 30 min at room temperature. The product was filtered off with suction and dried under high vacuum.

Yield: 9.6 g (96% of theory) of hentriacont-30-yn-1-ol.

$C_{31}H_{60}O$ (448.8) MS (DCI) 449M+H

EXAMPLE 11

1-t-Butyldimethylsilyloxyhentriacont-30-yne 9.6 g (0.0214 mol) of hentriacont-30-yn-1-ol of Example 10 were stirred vigorously in a mixture of 100 ml of chloroform and 4.4 ml of triethylamine for 1 h at room temperature. 3.5 g (0.0235 mol) of t-butyldimethylsilyl chloride were added, followed by a catalytic amount (spatula tipful) of 4-dimethylaminopyridine. The mixture was left to stand overnight at room temperature and half the solvent was stripped off. The remaining solution was chromatographed on a silica gel column (chloroform).

Yield: 8.7 g (73% of theory) of 1-t-butyldimethylsilyl-oxyhentriacont-30-yne.

$C_{37}H_{74}OSi$ (563.1) MS (DCI) 448M–$Me_2Si$ t-Bu+H; MS (EI) 563M+H

EXAMPLE 12

1-t-Butyldimethylsilyloxyundec-10-yne 1-t-Butyldimethylsilyloxyundec-30-yne was obtained analogously to Example 11.

$C_{17}H_{34}OSi$ (282.5) MS (EI) 283M+H

3. Reaction of acetylene derivatives III with ketones II to give the addition products IV

EXAMPLE 13

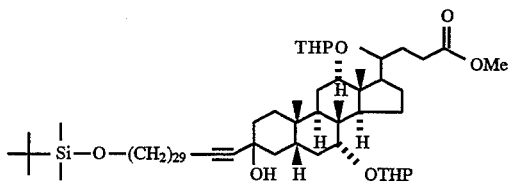

10.0 g (0.0178 mol) of 1-t-butyldimethylsilyloxyhentriacont-30-yne of Example 11 were placed in 100 ml of THF under an argon atmosphere.

11.1 ml (0.0178 mol) of n-butyllithium in hexane were added dropwise at room temperature. The mixture was refluxed for 1 h. 5.23 g (0.0089 mol) of methyl 3-keto-7, 12-ditetrahydropyranylcholate of Example 5, dissolved in 10 ml of THF, were added dropwise at room temperature. The reaction mixture was stirred for 1 h at room temperature, poured into 25% aqueous sodium dihydrogenphosphate solution and extracted with ethyl acetate (3×). Drying ($Na_2SO_4$) of the combined phases, stripping of the solvent and flash chromatography on silica gel (ethyl acetate/cyclohexane=1:9→1:5) gave 2.0 g (20%) of the 3β-OH isomer and 6.5 g (64%) of the 3α-OH isomer. Total yield: 8.5 g (84% of theory).

$C_{72}H_{130}O_8Si$ (1151.9) MS (FAB) 1158M+Li

EXAMPLE 14

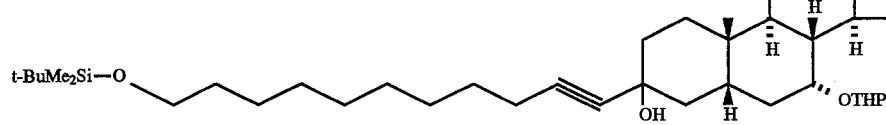

The compound indicated above was obtained analogously to Example 13. Yield based on 5.0 g of methyl 3-keto-7,12-ditetrahydropyranylcholate of Example 5: 1.0 g (9%) of the 3β-OH isomer and 8.4 g (72%) of the 3α-OH isomer. In contrast to the preparation of the compound obtained in Example 13, the n-butyllithium was added dropwise at −60° C. and the methyl 3-keto-7,12-ditetrahydropyranylcholate of Example 5 was added at −60° C. The reaction took place over 3 h at between −60° C. and −10° C.

$C_{52}H_{30}O_8Si$ (871.4) MS (FAB) 877M+Li

EXAMPLE 15

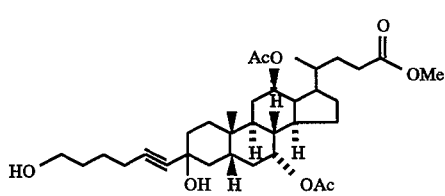

The compound indicated above was obtained analogously to Examples 13 and 14. 15.0 g of methyl 3-keto-7,12-diacetylcholate of Example 6 and 3 equivalents of hex-5-yn-1-ol gave 3.0 g (17%) of the 3β-OH isomer and 10.1 g (56%) of the 3α-OH isomer.

Total yield: 13.1 g (73% of theory).

The following changes were made compared with Example 13: 3 equivalents of hex-5-yn-1-ol and the corresponding number of equivalents of n-butyllithium were used. The n-butyllithium was added dropwise at −30° C. After the addition of methyl 3-keto-1,12-diacetylcholate of Example 6 at −30° C., the reaction took place at −30° C. over 4 h.

$C_{35}H_{54}O_8$ (602.8) MS (FAB) 609M+Li

EXAMPLE 16

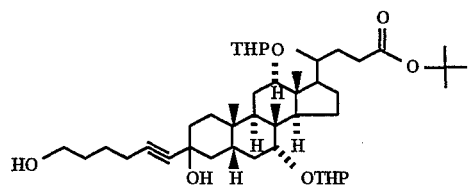

The compound indicated above was obtained analogously to Example 15.

Total yield (3α-OH and 3β-OH isomers): 88% of theory.

$C_{44}H_{72}O_8$ (729) MS (FAB) 735M+Li

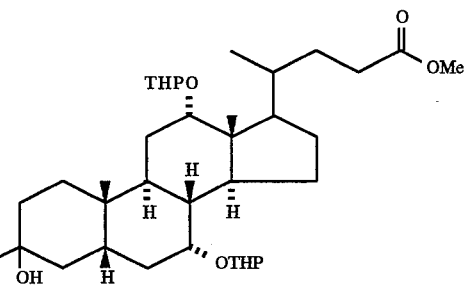

EXAMPLE 17

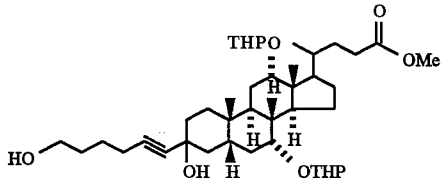

The compound indicated above was obtained analogously to Example 16. 12.0 g of methyl 3-keto-7,12-ditetrahydropyranylcholate of Example 5 gave the compound indicated above in 77% yield.

$C_{41}H_{66}O_8$ (687.0) MS (FAB) 693M+Li

4. Conversion of the addition products IV to compounds I according to the invention

EXAMPLE 18

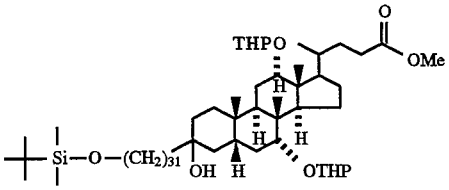

6.2 g (0.0054 mol) of the 3α-OH isomer of the compound of Example 13 were dissolved in 100 ml of ethyl acetate and 10 ml of triethylamine and hydrogenated in the presence of a catalytic amount of Pd/C (10%) at room temperature and normal pressure. When the hydrogen uptake had ended, 200 ml of chloroform were added and the catalyst was filtered off. Stripping of the solvent under vacuum gave the compound indicated above in quantitative yield.

$C_{72}H_{134}O_8Si$ (1155.9) MS (FAB) 1162M+Li

The Examples in Table 1 were carried out analogously to Example 18.

TABLE 1

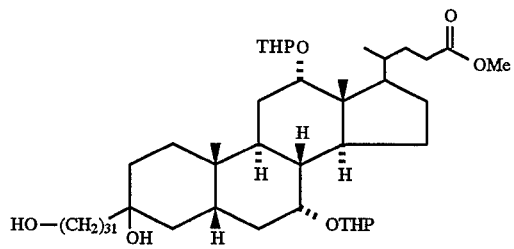

| Example | $X^1$ | $X^2 = X^3$ | Y | n | Isomer | Starting material | Empirical formula (molar mass) | MS (FAB) |
|---|---|---|---|---|---|---|---|---|
| 19 | OSi t-BuMe$_2$ | OTHP | OCH$_3$ | 29 | 3β-OH | 13 | $C_{72}H_{134}O_8Si$ (1155.9) | 1162 M + Li |
| 20 | OSi t-BuMe$_2$ | OTHP | OCH$_3$ | 9 | 3α-OH | 14 | $C_{52}H_{94}O_8Si$ (875.4) | 881 M + Li |
| 21 | OSi t-BuMe$_2$ | OTHP | OCH$_3$ | 9 | 3β-OH | 14 | $C_{52}H_{94}O_8Si$ (875.4) | 881 M + Li |
| 22 | OH | OAc | OCH$_3$ | 4 | 3α-OH | 15 | $C_{35}H_{58}O_8$ (606.8) | 613 M + Li |
| 23 | OH | OAc | OCH$_3$ | 4 | 3β-OH | 15 | $C_{35}H_{58}O_8$ (606.8) | 613 M + Li |
| 24 | OH | OTHP | OCH$_3$ | 4 | 3α-OH | 17 | $C_{41}H_{70}O_8$ (691.0) | 697 M + Li |
| 25 | OH | OTHP | OCH$_3$ | 4 | 3β-OH | 17 | $C_{41}H_{70}O_8$ (691.0) | 697 M + Li |
| 26 | OH | OTHP | Ot—Bu | 4 | 3α-OH | 16 | $C_{44}H_{72}O_8$ (729.1) | 735 M + Li |
| 27 | OH | OTHP | Ot—Bu | 4 | 3β-OH | 16 | $C_{44}H_{72}O_8$ (729.1) | 735 M + Li |

EXAMPLE 28

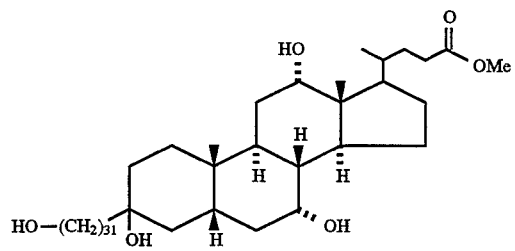

6.3 g of the compound obtained in Example 18 were dissolved in 75 ml of THF and stirred overnight at room temperature with 5.1 g (0.0161 mol) of tetrabutylammonium fluoride trihydrate. The reaction mixture was poured into water and extracted with chloroform (3×) and the combined organic phases were dried (Na$_2$SO$_4$). Removal of the solvent gave the compound indicated above in quantitative yield.

$C_{66}H_{120}O_8$ (1041.7) MS (FAB) 1047M+Li

EXAMPLE 29

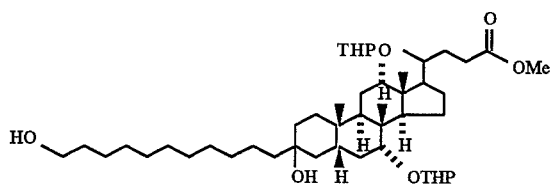

The compound indicated above was obtained from the compound of Example 20 analogously to Example 28.

$C_{46}H_{80}O_8$ MS (FAB) 767M+Li

EXAMPLE 30

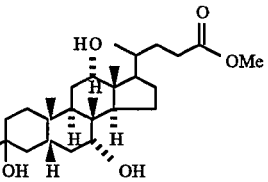

3.1 g of the compound obtained in Example 28 were dissolved in a mixture of 10 ml of chloroform and 5 ml of methanol, and a catalytic amount (spatula tipful) of p-toluenesulfonic acid monohydrate was added. The mixture was left to stand overnight at room temperature and the solvent was stripped off. Flash chromatography on silica gel (chloroform/methanol=5:1) gave 1.7 g (72% of theory) of the compound indicated above.

$C_{56}H_{104}O_6$ (873.4) MS (FAB) 879M+Li

EXAMPLE 31

The compound indicated above was obtained from the compound of Example 29 analogously to Example 30.

$C_{36}H_{64}O_6$ (592.9) MS (FAB) 599M+Li

EXAMPLE 32/1

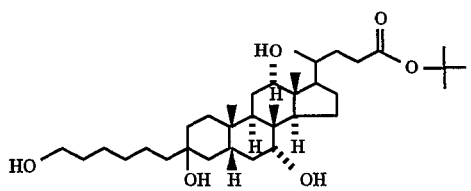

1.4 g (0.0019 mol) of the compounds obtained in Examples 26 and 24 as a 3α-OH/3β-OH isomer mixture were dissolved in 25 ml of methanol, and 50 mg of p-toluenesulfonic acid monohydrate were added at room temperature. After 5 h at room temperature, the mixture was poured into saturated aqueous NaHCO$_3$ solution. Extraction with ethyl acetate (3×), drying of the combined phases (Na$_2$SO$_4$), stripping of the solvent and column chromatography on silica gel (ethyl acetate→ethyl acetate/methanol= 9:1) gave 165 mg (15%) of the 3β-OH isomer and 684 mg (63%) of the 3α-OH isomer. Total yield: 78% of theory of the compound indicated above.

$C_{34}H_{60}O_6$ (564.8) MS (FAB) 571M+Li

EXAMPLE 32/2

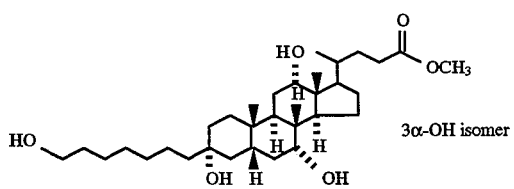

3α-OH isomer

The compound indicated above and the corresponding 3β-OH isomer were obtained from the compounds of Examples 22/23 analogously to Example 32/1. 8.7 g of starting material gave 1.01 g (14%) of the 3β-OH isomer and 4.26 g (57%) of the 3α-OH isomer. Total yield: 71% of theory of the compound indicated above.

$C_{31}H_{54}O_6$ (522.7) MS (ES+) 529M+Li

EXAMPLE 33

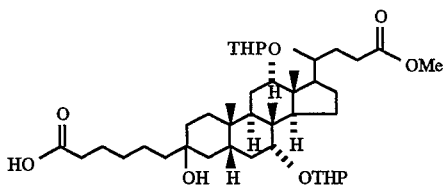

9.2 g (0.0133 mol) of an isomer mixture of the compounds obtained in Examples 24 and 25 were placed in a mixture of 75 ml of carbon tetrachloride, 75 ml of acetonitrile and 100 ml of water at room temperature, 14.2 g (0.0666 mol) of sodium periodate and 100 mg of ruthenium(III) chloride (as catalyst) were added and the reaction mixture was stirred for 3 h at room temperature. It was extracted 3× with methylene chloride and the combined organic phases were dried. Stripping of the solvent under vacuum and flash chromatography on silica gel (ethyl acetate/cyclohexane=1:1) gave 7.5 g (80% of theory) of the compound indicated above as a mixture of the 3α-OH and 3β-OH isomers.

$C_{41}H_{68}O_9$ (705.0) MS (FAB) 711M+Li

The following Examples were carried out analogously to Example 33:

EXAMPLE 34

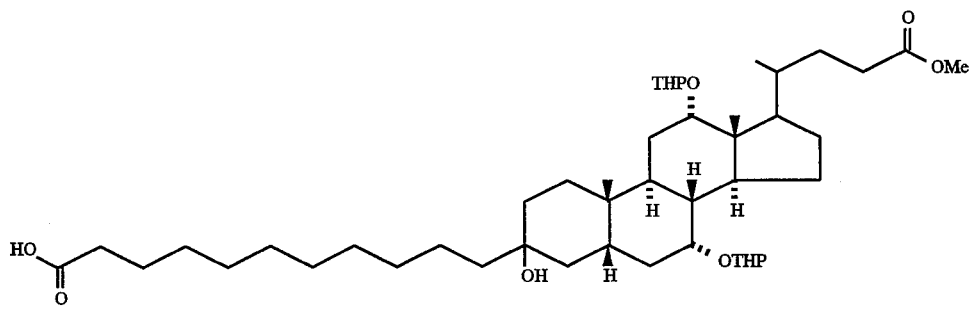

EXAMPLE 35

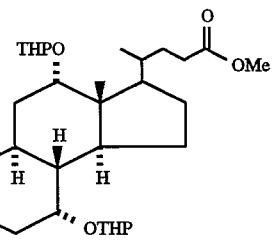

EXAMPLE 36

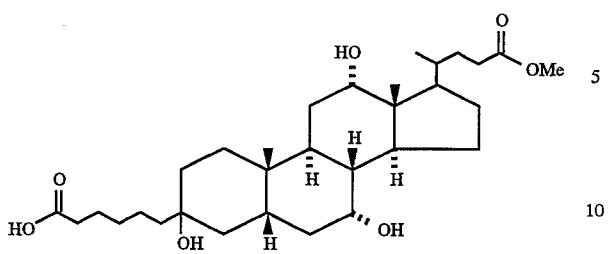

800 mg (0.00114 mol) of the compound obtained as an isomer mixture in Example 33 were placed in a mixture of 5 ml of THF, 15 ml of acetonitrile and 5 ml of water, and a catalytic amount (spatula tipful) of p-toluenesulfonic acid monohydrate was added. After 16 h at room temperature, the reaction mixture was poured into water and extracted 3× with methylene chloride. The combined organic phases were dried ($Na_2SO_4$) and the solvent was removed. Flash chromatography on silica gel (ethyl acetate→ethyl acetate/ MeOH=9:1) gave 110 mg (18%) of the 3β-OH isomer and 357 mg (59%) of the 3α-OH isomer. Total yield: 467 mg (77% of theory) of the compound indicated above.

$C_{31}H_{52}O_7$ (536.7) MS (FAB) 543M+Li, 549M+2Li-H

EXAMPLE 37

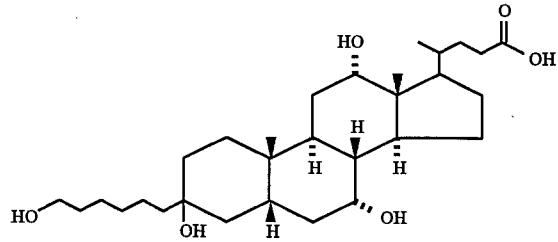

5.0 g (0.0082 mol) of the isomer mixture obtained in Examples 22 and 23 were dissolved in 50 ml of ethanol and stirred overnight at room temperature with 100 ml of molar aqueous sodium hydroxide solution. The reaction mixture was poured into 25% aqueous $NaH_2PO_4$ and extracted 3× with ethyl acetate. The combined organic phases were dried ($Na_2SO_4$). Stripping of the solvent gave 4.1 g (98% of theory) of the free acid of the formula indicated above.

$C_{30}H_{52}O_6$ (508.7) MS (ES+) 515M+Li

EXAMPLE 38

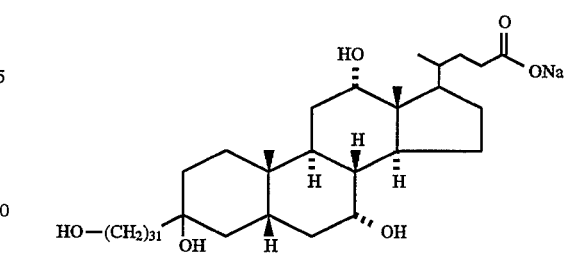

The compound indicated above was obtained analogously to Example 37 from the compound prepared in Example 30. In contrast to the instructions given in Example 37, a mixture of THF and methanol (2:1) was used as the solvent in Example 38, the sodium salt crystallizing out.

Yield: 270 mg (89% of theory) from 300 mg of the compound obtained in Example 30.

$C_{55}H_{101}O_6Na$ (881.4) MS (FAB) 881M+H, 903M+Na

The free acid can be obtained by acidification with HCl.

EXAMPLE 39

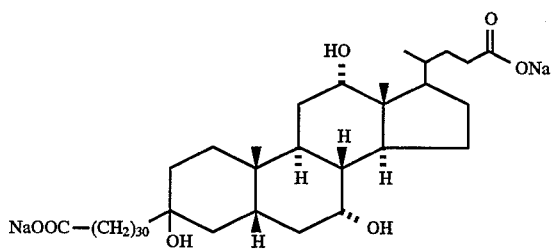

1.5 g (1.4 mol) of the compound obtained in Example 35 were placed in a mixture of 40 ml of THF and 20 ml of methanol, a catalytic amount (spatula tipful) of p-toluenesulfonic acid was added and the mixture was stirred for 18 h at room temperature. 5 ml of 2N aqueous sodium hydroxide solution were then added and the mixture was stirred overnight. The disodium salt which precipitated out was filtered off with suction and washed with methanol and diisopropyl ether.

Yield: 800 mg (61% of theory) of the compound indicated above.

$C_{55}H_{98}O_7Na_2$ (917.4) MS (FAB) 917 (M+H), 939 (M+Na)

The free acid can be obtained by acidification with dilute hydrochloric acid.

EXAMPLE 40

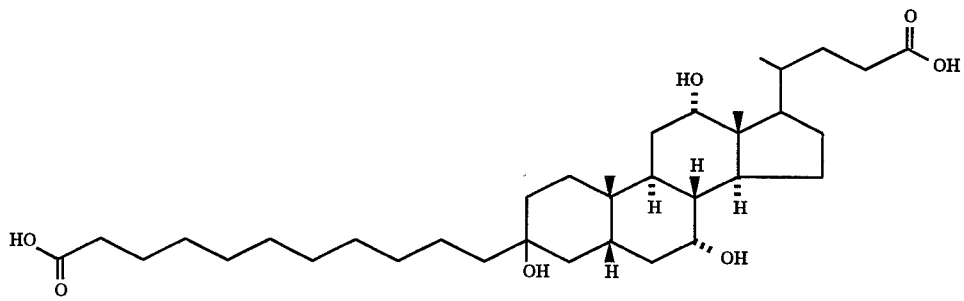

500 mg (0.65 mmol) of the compound obtained in Example 34 were stirred in 20 ml of methanol for 5 h at room temperature, a spatula tipful of p-toluenesulfonic acid monohydrate being added. 3.2 ml of 1N aqueous sodium hydroxide solution were then added and the reaction mixture was left to stand overnight. It was poured into 10% aqueous NaH$_2$PO$_4$ solution and stirred for 30 min. The product was filtered off with suction, washed with water and dried under high vacuum.

Yield: 360 mg (94% of theory) of the compound indicated above.

C$_{35}$H$_{60}$O$_7$ (592.9) MS (FAB) 615M+Na–H

EXAMPLE 41

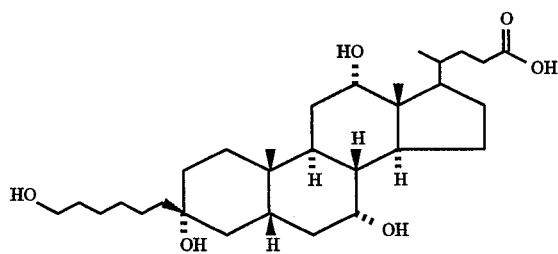

5 g (7.71 mmol) of the 3α-OH isomer obtained in Example 22 were dissolved in 100 ml of ethanol, and 200 ml of 5 molar aqueous sodium hydroxide solution were added at room temperature. After 18 h, the reaction mixture was poured into 500 ml of 25% aqueous NaH$_2$PO$_4$ solution. Extraction with ethyl acetate (3×), drying (Na$_2$SO$_4$) of the combined organic phases and removal of the solvent gave a quantitative yield of 3.95 g of the compound indicated above.

C$_{30}$H$_{52}$O$_6$ (508.6) MS (FAB) 515M+Li, 521M+2Li–H

The 3β-OH isomer was prepared by the corresponding procedure.

EXAMPLE 42

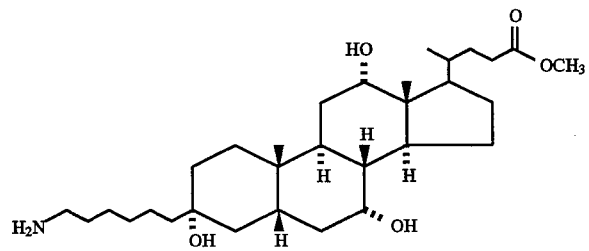

4.2 g (8.04 mmol) of the pure 3α-OH isomer obtained in Example 32/2 were placed in 25 ml of pyridine. 775 μl (9.81 mmol) of methanesulfonyl chloride were added dropwise at 0° C. and the reaction mixture was stirred for 2 h at 0° C. It was poured into ice-water and extracted 3× with ethyl acetate. The combined organic phases were dried (Na$_2$SO$_4$) and concentrated to give a quantitative yield of 4.8 g, based on the mesylate of Example 32/2.

This material (4.8 g) was stirred in 50 ml of DMF for 2.5 h at 80° C. in the presence of 6.3 g of potassium phthalimide. After cooling, the mixture was poured into water and extracted 3× with ethyl acetate. Drying of the combined organic phases (Na$_2$SO$_4$), stripping of the solvent and chromatography on silica gel (ethyl acetate) gave 5.02 g (96% of theory) of the corresponding phthalimide derivative.

4.9 g (7.52 mmol) of the phthalimide derivative were dissolved in 100 ml of methanol. 10.7 ml of hydrazine hydrate were added dropwise at room temperature. After stirring for 1.5 h at room temperature, the mixture was acidified with 2N aqueous hydrochloric acid and neutralized with saturated aqueous NaHCO$_3$ solution. Extraction three times with ethyl acetate, drying of the combined organic phases (Na$_2$SO$_4$), stripping of the solvent, extraction of the residue by stirring (with ethyl acetate/n-heptane=2:1), filtration with suction and drying under high vacuum gave 3.78 g (96% of theory) of the compound indicated above.

C$_{31}$H$_{55}$NO$_5$ (521.7) MS (FAB) 528M+Li

EXAMPLE 43

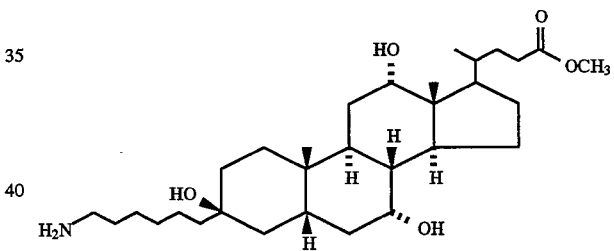

The 3β-OH isomer was prepared as indicated above, analogously to Example 42, from the pure 3β-OH isomer obtained in Example 32/2.

C$_{31}$H$_{55}$NO$_5$ (521.7) MS (FAB) 522M+H, 528M+Li

EXAMPLE 44

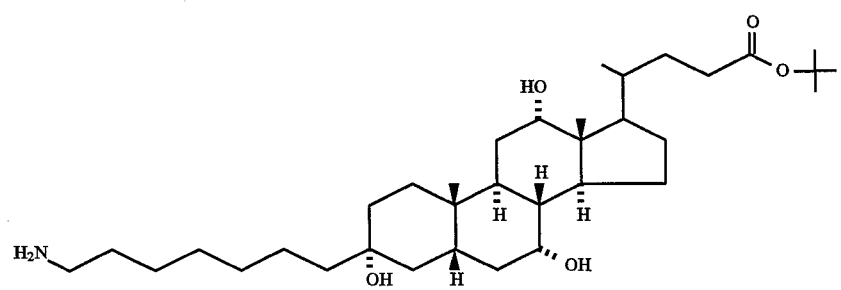

The 3αOH is was obtained as indicated above, analogously to Example 42, from the pure 3α-OH isomer prepared in Example 32/1.

$C_{34}H_{61}NO_5$ (563.8) MS (FAB) 570M+Li

EXAMPLE 45

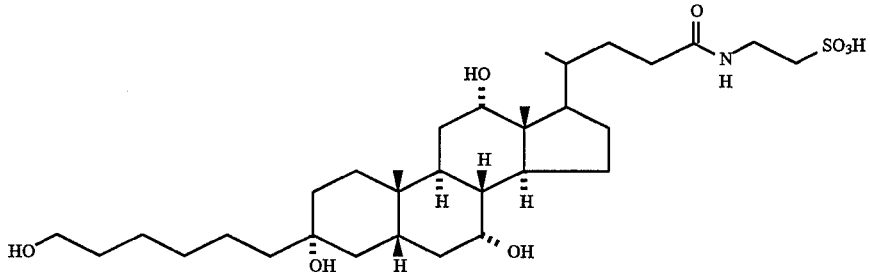

102 mg (0.2 mmol) of the 3α-OH isomer obtained in Example 41 were placed in a mixture of 5 ml of THF and 0.5 ml of $NEt_3$ at 0° C. 30 µl (0.3 mmol) of ethyl chloroformate were added dropwise and the mixture was stirred for 15 min at 0° C. A solution of 88 mg (0.7 mmol) of taurine in 0.1N aqueous sodium hydroxide solution was then added and the mixture was stirred for 1 h at room temperature. Aqueous $NaH_2PO_4$ solution was added, the phases were separated and the aqueous phase was extracted 2× with THF. The combined organic phases were dried ($Na_2SO_4$). Removal of the solvent and trituration of the residue with ethyl acetate/ n-heptane gave 113 mg (92%) of the compound indicated above.

$C_{32}H_{57}NO_8S$ (615.8) MS (ES-) 614M-H

EXAMPLE 46

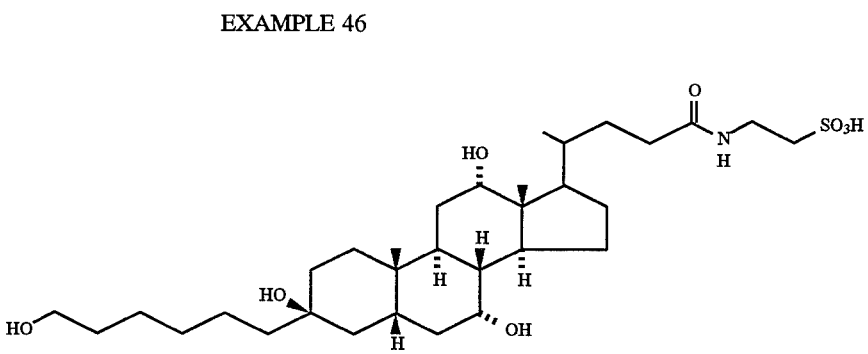

The compound indicated above was prepared analogously to Example 45 from the 3β-OH isomer of the compound obtained in Example 41.

$C_{32}H_{57}NO_8S$ (615.8) MS (ES-) 614 n—H

We claim:

1. A linker-modified bile acid derivative of the formula I:

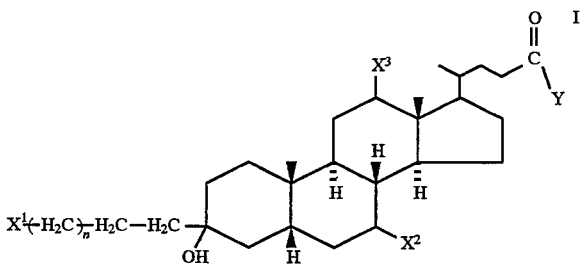

wherein

| $X^1$ is | |
|---|---|
| $CH_2OH$, | where Sil is a silyl protecting group |
| $CH_2NH_2$, | of the formula |
| $CH_2OSil$, | $SiMe_3$, |
| | $SiMe_2t$-Bu or |
| | $SiPh_2t$-Bu, |
| $CH_2OTHP$, | where phenyl can be substituted by |
| $CH_2OCH_2Ph$, | p-methoxy, |
| $CH_2O$-trityl, | where acyl is a linear or branched |
| $CH_2O$-acyl, | radical having 2 to 8 carbon atoms, |
| $CH_2O$-benzoyl, | where the aromatic ring can also be monosubstituted to trisubstituted by a linear or branched $C_1$-$C_4$-alkyl radical, $OCH_3$, F or Cl, |

-continued

| | |
|---|---|
| CH$_2$OCHO, CH$_2$OC(O)OCH$_2$Ph, CH$_2$NH-acyl, | where acyl is a linear or branched radical having 2 to 8 carbon atoms, |
| CH$_2$NH-benzoyl, | where the aromatic ring can also be monosubstituted to trisubstituted by a linear or branched C$_1$–C$_4$-alkyl radical, OCH$_3$, F or Cl, |
| CH$_2$N(CH$_2$Ph)$_2$, | where the aromatic rings can also be monosubstituted to trisubstituted by a linear or branched C$_1$–C$_4$-alkyl radical, OCH$_3$, F or Cl, |
| CH$_2$O—CH$_2$—CH=CH$_2$, CO$_2$H, CO$_2$M, | where M is an alkali metal or alkaline earth metal, |
| CO$_2$N(X$^4$)$_4$, | where X$^4$ is identical or different and is an H atom or a linear or branched alkyl radical having 1 to 8 carbon atoms, |
| or CO$_2$X$^5$, | where X$^5$ is methyl, ethyl, alkyl or benzyl; |

$X^2$ and $X^3$ are identical or different radicals selected from the group consisting of

| | |
|---|---|
| H, OH, OTHP, OAc, SiMe$_3$, OSiMe$_2$t-Bu, SiPh$_2$t-Bu, OCH$_2$Ph, | where the phenyl group can also be monosubstituted to trisubstituted by a linear or branched C$_1$–C$_4$-alkyl radical, OCH$_3$, F or Cl, |
| O—CH$_2$CH=CH$_2$, OC(O)CH$_2$Ph, | where the phenyl group can also be monosubstituted to trisubstituted by a linear or branched C$_1$–C$_4$-alkyl radical, OCH$_3$, F or Cl, |
| OC(O)Ph, | where the phenyl group can also be monosubstituted to trisubstituted by a linear or branched C$_1$–C$_4$-alkyl radical, OCH$_3$, F or Cl, |
| and OC(O)O-alkyl, | | the radical $X^2$ being located in the α- or β-position and the radical $X^3$ only in the α-position;
Y is

| | |
|---|---|
| OH, | a linear or branched alkoxy radical having 1 to 8 carbon atoms, |
| O—CH$_2$Ph, | where the phenyl group can also be monosubstituted to trisubstituted by a linear or branched C$_1$–C$_4$-alkyl radical, OCH$_3$, F or Cl, |
| O-Ph, | where the phenyl group can also be monosubstituted to trisubstituted by a linear or branched C$_1$–C$_4$-alkyl radical, OCH$_3$, F or Cl, |
| OM$^1$, | where M$^1$ is an alkali metal, |
| ONX$_4^6$, | where X$^6$ is an H atom or a C$_1$–C$_8$-alkyl group, |
| OTHP, OCH$_2$—CH=CH$_2$, NH$_2$, NH(CH$_2$)$_2$SO$_3$H, N(CH$_3$)(CH$_2$)$_2$SO$_3$H, NHCH$_2$CO$_2$H or N(CH$_3$)CH$_2$CO$_2$N; | | the hydroxyl group in ring position C-3 can be located in either the α- or β-position and n is equal to 0 to 47.

2. A bile acid derivative of the formula I as claimed in claim 1, wherein
$X^1$ is
CH$_2$OH,
CH$_2$NH$_2$,
CH$_2$OSiMe$_2$t-Bu,
CH$_2$OTHP,
CO$_2$H or
CO$_2$CH$_3$;

$X^2$ and $X^3$ are identical or different radicals selected from the group consisting of
H,
OH,
OAc and
OTHP, the radical $X^2$ being located in the α- or β-position and the radical $X^3$ only in the α-position;
Y is
OH,
OCH$_3$ or
Ot-Bu;

the hydroxyl group in ring position C-3 is located in the α-position and n is equal to 0 to 47.

3. A process for the preparation of bile acid derivatives of the formula I as claimed in claim 1, which comprises reacting a bile acid ketone of the formula II:

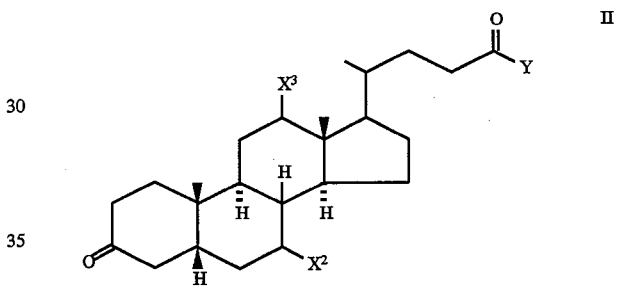

with a compound of the formula III:

HC≡C—(CH$_2$)$_n$—X$^1$    (III)

after conversion to the acetylide with a strong base, to give an addition product of the formula IV:

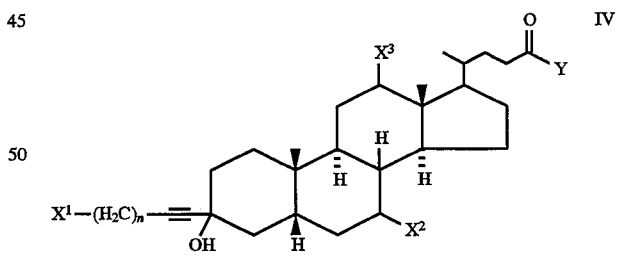

which is then converted by Pd/C-catalyzed hydrogenation to a compound of the formula I:

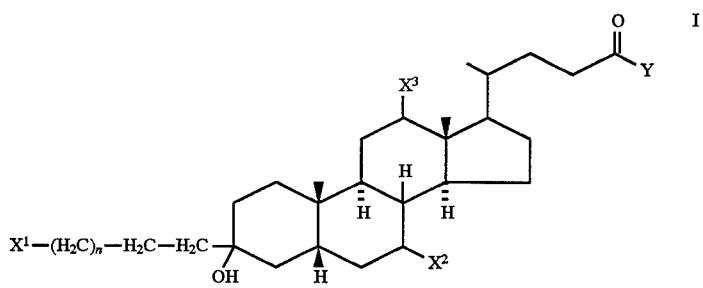

wherein, in the formulae, the radicals $X^1$, $X^2$, $X^3$ and Y and n are as defined in claim 1.

4. A pharmaceutical composition containing at least one bile acid derivative of the formula I as claimed in claim 1, and a pharmaceutically acceptable carrier.

5. A hypolipidemic containing a bile acid derivative of the formula I as claimed in claim 1.

6. A method of treating a host in need of a hypolipidemic agent comprising:

administering to said host a bile acid derivative of the formula I as claimed in claim 1.

* * * * *

UNITED STATES PATENT AND TRADEMARK OFFICE
CERTIFICATE OF CORRECTION

PATENT NO. : 5,641,767
DATED : June 24, 1997
INVENTOR(S) : Günther Wess et al.

It is certified that error appears in the above-identified patent and that said Letters Patent is hereby corrected as shown below:

On the Title page, Item [57], in the Abstract line 7, (excluding formula I) change "pldemics" to --pidemics--.

Claim 1, columns 24-25, line 36, Text in right hand columns should be aligned with chemical groups on left hand side of columns as follows:

wherein
$X^1$ is
    $CH_2OH$,
    $CH_2NH_2$,
    $CH_2OSil$,        where Sil is a silyl protecting group of the formula
                                $SiMe_3$,
                                $SiMe_2t$-Bu or
                                $SiPh_2t$-Bu,
    $CH_2OTHP$,
    $CH_2OCH_2Ph$,    where phenyl can be substituted by p- methoxy,

UNITED STATES PATENT AND TRADEMARK OFFICE
CERTIFICATE OF CORRECTION

PATENT NO. : 5,641,767
DATED : June 24, 1997
INVENTOR(S) : Gunther Wess, et al

It is certified that error appears in the above-identified patent and that said Letters Patent is hereby corrected as shown below:

$CH_2O$-trityl, $CH_2O$-acyl,     where acyl is a linear or branched radical having 2 to 8 carbon atoms, $CH_2O$-benzoyl,     where the aromatic ring can also be monosubstituted to trisubstituted by a linear or branched $C_1$-$C_4$-alkyl radical, $OCH_3$, F or Cl, $CH_2OCHO$, $CH_2OC(O)OCH_2Ph$,

UNITED STATES PATENT AND TRADEMARK OFFICE
CERTIFICATE OF CORRECTION

PATENT NO. : 5,641,767
DATED : June 24, 1997
INVENTOR(S) : Gunther Wess, et al

It is certified that error appears in the above-identified patent and that said Letters Patent is hereby corrected as shown below:

| | |
|---|---|
| $CH_2NH$-acyl, | where acyl is a linear or branched radical having 2 to 8 carbon atoms, |
| $CH_2NH$-benzoyl, | where the aromatic ring can also be monosubstituted to trisubstituted by a linear or branched $C_1$-$C_4$-alkyl radical, $OCH_3$, F or Cl, |
| $CH_2N(CH_2Ph)_2$, | where the aromatic rings can also be monosubstituted to trisubstituted by a linear or branched $C_1$-$C_4$-alkyl radical, $OCH_3$, F or Cl, |

UNITED STATES PATENT AND TRADEMARK OFFICE
CERTIFICATE OF CORRECTION

PATENT NO. : 5,641,767
DATED : June 24, 1997
INVENTOR(S) : Gunther Wess, et al

It is certified that error appears in the above-identified patent and that said Letters Patent is hereby corrected as shown below:

$CH_2O-CH_2-CH=CH_2$, $CO_2H$, $CO_2M$, where M is an alkali metal or alkaline earth metal, $CO_2N(X^4)_4$, where $X^4$ is identical or different and is an H atom or a linear or branched alkyl radical having 1 to 8 carbon atoms, or $CO_2X^5$, where $X^5$ is methyl, ethyl, alkyl or benzyl;

UNITED STATES PATENT AND TRADEMARK OFFICE
CERTIFICATE OF CORRECTION

PATENT NO. : 5,641,767
DATED : June 24, 1997
INVENTOR(S) : Gunther Wess, et al

It is certified that error appears in the above-identified patent and that said Letters Patent is hereby corrected as shown below:

$X^2$ and $X^3$ are identical or different radicals selected from the group consisting of
- H,
- OH,
- OTHP,
- OAc,
- $SiMe_3$,
- $OSiMe_2$t-Bu,
- $SiPh_2$t-Bu,
- $OCH_2Ph$, where the phenyl group can also be

UNITED STATES PATENT AND TRADEMARK OFFICE
CERTIFICATE OF CORRECTION

PATENT NO. : 5,641,767
DATED : June 24, 1997
INVENTOR(S) : Gunther Wess, et al

It is certified that error appears in the above-identified patent and that said Letters Patent is hereby corrected as shown below:

|  |  |
|---|---|
|  | monosubstituted to trisubstituted by a linear or branched $C_1$-$C_4$-alkyl radical, $OCH_3$, F or Cl, |
| $O-CH_2CH=CH_2$, |  |
| $OC(O)CH_2Ph$, | where the phenyl group can also be monosubstituted to trisubstituted by a linear or branched $C_1$-$C_4$-alkyl radical, $OCH_3$, F or Cl, |
| $OC(O)Ph$, | where the phenyl group can also be monosubstituted to trisubstituted by a linear or branched $C_1$-$C_4$-alkyl radical, $OCH_3$, F or Cl, | and $OC(O)O$-alkyl, the radical $X^2$ being located in the $\alpha$- or $\beta$-position and the radical $X^3$ only in the $\alpha$-position;

UNITED STATES PATENT AND TRADEMARK OFFICE
CERTIFICATE OF CORRECTION

PATENT NO. : 5,641,767
DATED : June 24, 1997
INVENTOR(S) : Gunther Wess, et al

It is certified that error appears in the above-identified patent and that said Letters Patent is hereby corrected as shown below:

```
Y is
    OH,
    a linear or branched alkoxy radical having 1 to
8 carbon atoms,
```

Signed and Sealed this

Fourth Day of April, 2000

Attest:

Q. TODD DICKINSON

Attesting Officer

Director of Patents and Trademarks